United States Patent [19]

Giordano et al.

[11] Patent Number: 5,554,228
[45] Date of Patent: Sep. 10, 1996

[54] METHOD AND DEVICE FOR CLEANING MEDICAL INSTRUMENTS

[75] Inventors: Nicola Giordano, Villingen-Schwenningen; Dieter Weisshaupt, Immendingen, both of Germany

[73] Assignee: Aesculap AG, Tuttlingen, Germany

[21] Appl. No.: 356,398

[22] PCT Filed: Apr. 13, 1993

[86] PCT No.: PCT/EP93/00889

§ 371 Date: Dec. 15, 1994

§ 102(e) Date: Dec. 15, 1994

[87] PCT Pub. No.: WO94/00068

PCT Pub. Date: Jan. 6, 1994

[30] Foreign Application Priority Data

Jun. 26, 1992 [DE] Germany ............ 42 21 102.6

[51] Int. Cl.$^6$ .................... B08B 3/04; B08B 5/04
[52] U.S. Cl. .................... 134/21; 134/22.11; 134/24; 134/25.1; 134/32; 134/34; 134/42; 134/169 R; 134/170
[58] Field of Search .................... 134/21, 22.11, 134/24, 25.1, 32, 34, 42, 169 R, 170

[56] References Cited

U.S. PATENT DOCUMENTS

| | | | |
|---|---|---|---|
| 3,956,011 | 5/1976 | Carleton | 134/21 |
| 4,352,361 | 10/1982 | Chester | 134/58 R |
| 4,412,531 | 11/1983 | Chikashige | 128/4 |
| 5,090,433 | 2/1992 | Kamaga | 134/169 C |

FOREIGN PATENT DOCUMENTS

| | | |
|---|---|---|
| 345228 | 12/1989 | European Pat. Off. . |
| 483059 | 4/1992 | European Pat. Off. . |
| 2929804 | 2/1981 | Germany . |
| 3232329 | 3/1984 | Germany . |
| 3416743 | 7/1985 | Germany . |
| 4102138 | 10/1991 | Germany . |
| 1168035 | 10/1969 | United Kingdom . |

*Primary Examiner*—Zeinab El-Arini
*Attorney, Agent, or Firm*—Barry R. Lipsitz

[57] ABSTRACT

A medical tubular shaft instrument with a channel-like cavity is cleaned by drawing a cleaning liquid through the cavity by vacuum suction. The instrument is placed into a holder in a container where one end of the instrument is dipped into a cleaning liquid held in the container. The other end of the instrument is connected to a suction line. A flushing action in the interior of the cavity is created which removes impurities residing there. A device is also proposed which can clean one or several instruments at the same time, and can be folded to a more compact position when not in use.

20 Claims, 4 Drawing Sheets

METHOD AND DEVICE FOR CLEANING MEDICAL INSTRUMENTS

BACKGROUND OF THE INVENTION

The invention relates to a method for cleaning medical instruments having a channel-like cavity as well as to a device for carrying out this method, comprising a container for a cleaning liquid, into which the instruments dip.

Medical instruments must be thoroughly cleaned after their use, in particular body fluids left in the instruments must be removed completely from the instruments before these are sterilized.

It has proven to be difficult to carry out such a thorough preliminary cleaning of instruments which have narrow, in particular channel-like cavities, above all when other parts are arranged in addition in the cavities, for example draw rods, cables etc., so that it is impossible to penetrate into the interior of the cavities with cleaning brushes. Thus, difficulties have resulted during the cleaning of so-called tubular shaft instruments, i.e. instruments having very narrow, long, sleeve-like channels, such as, for example, those used in the form of biopsy forceps.

SUMMARY OF THE INVENTION

The object of the invention is to improve a method of the type described at the outset such that a reliable cleaning can also take place in the case of instruments of this type.

This object is accomplished in accordance with the invention, in a method of the type described at the outset, in that the instruments are dipped into a cleaning liquid with one end of the cavity and the cavity is connected at the other end to a suction line. In this way, cleaning liquid is drawn through the cavity by suction and thereby cleans even the smallest gaps from impurities located therein; at the same time, these impurities are also drawn off by suction.

In this respect, it is favorable for several instruments to be connected simultaneously to a common suction line and for each connection between an instrument and the suction line to be opened or closed individually. This means that it is possible to clean a greater number of such instruments at the same time with the same suction source. As soon as an instrument is clean, the connection associated with this instrument is closed so that operations with such a device as a whole can be continued while the precleaned instrument is removed.

It is favorable for the instrument to be dipped into the cleaning liquid to such a depth that all the openings of the cavity are arranged beneath the level of the liquid except for the suction opening of the cavity. In this way, it is possible for cleaning liquid to be drawn in by suction not only through one opening of the channel-like instrument at the low-lying end but such a drawing-in by suction also takes place through all the other openings which are possibly present, for example through slits and gaps in joints etc. At the same time, this prevents infiltrated air being sucked in which could diminish the effectiveness of the washing of the instrument with the cleaning liquid.

On the other hand, in a modified embodiment it is possible for gas bubbles to be introduced into the cleaning bath, these bubbles rising in the cleaning liquid in the region of the suction openings of the cavity and thereby being drawn into the cavity by suction. Due to the rising gas bubbles, which are preferably air bubbles, a turbulence is generated in the cleaning liquid which also continues in the interior of the cavity since the bubbles are also drawn in by suction. This turbulence promotes the cleaning action of the cleaning liquid.

In addition, with instruments having parts movable relative to one another these parts can be moved relative to one another during the cleaning process. The relative movement of the parts of the instrument which are arranged to move relative to one another ensures that a particularly reliable cleaning takes place; in particular, particles are also washed out which could possibly become caught in stationary parts.

In a device of the type described at the outset, the specified object is accomplished in accordance with the invention in that at least one suction line is provided which is sealingly connectable to an opening of the cavity.

In this respect, it is favorable for several connections to be provided at a suction line for one instrument each and for a closure means to be associated with each connection.

In a preferred embodiment, the connection is formed by a hose connected to the suction line and this hose can be sealingly secured in position on the instrument. It is then sufficient, for example, to attach the hose sealingly to the one end of the tubular shaft instrument and, as for the rest, to dip the instrument into the cleaning liquid in order to cause the instrument to be flushed through completely merely by applying a vacuum to the hose.

The closure means can, for example, be a hand-operable closure valve. A special embodiment provides for the closure means to be a plug which is secured in position on the device and to which the hose can be sealingly attached with its free end.

According to a particularly preferred embodiment, a holder is provided, on which the instruments can be positioned such that they dip into the cleaning liquid at least partially.

The holder can bear the connections and the closure means at its upper end protruding out of the liquid.

In this respect, it is favorable for the holder to consist of at least two parts which are movable relative to one another between an operative position with a large overall height and an inoperative position with a low overall height. This means that it is possible to keep the holder in a small space even when relatively large instruments are intended to be held in it. In the operative position, the holder is, namely, suitable for the relatively large instruments with respect to its dimensions; in the inoperative position, on the other hand, the overall height of the holder is considerably reduced.

In this respect, it is favorable for the two parts to be securable relative to one another in the operative position, for example by a locking connection or a locking lever.

The upper part can, for example, be designed to be pivotable relative to the lower part of the holder.

A particularly space-saving arrangement results when a suction chamber is arranged in the upper part of the holder and this bears a number of closure valves next to one another, and when a hose is connected to each closure valve as connection to the instruments. The holder therefore combines the essential functions of the cleaning device so that a simple and space-saving component is created.

In a preferred embodiment, a container which can be filled with the cleaning liquid is provided and this can be closed by means of a cover and is dimensioned such that it accommodates the holder completely at least in the inoperative position. This means that the entire device, including the holder, can be accommodated in a closed container which is designed, for example, like a sterilizer and also corresponds in its dimensions to the dimensions of conventional sterilizers although instruments which possibly have larger dimensions can be cleaned in such a container.

It is favorable for a removable insert to be arranged in the container above the holder, the connection hoses being adapted to be placed in this insert. This results in a complete cleansing device in such a container which need merely be connected to a suction source, for example to a secretion suction means already customary in operating theaters.

In a preferred embodiment, it is provided in addition for at least one inlet for a gas to be provided in the container beneath the instruments dipping into the cleaning liquid, the gas entering the cleaning liquid beneath the instruments through this inlet.

A further, preferred embodiment is characterized by the fact that a drive engaging the instruments is provided, this drive moving relative to one another parts of the instruments which are movable relative to one another.

The following description of preferred embodiments of the invention serves to explain the invention in greater detail in conjunction with the drawings.

DETAILED DESCRIPTION OF THE INVENTION

Figure 1:
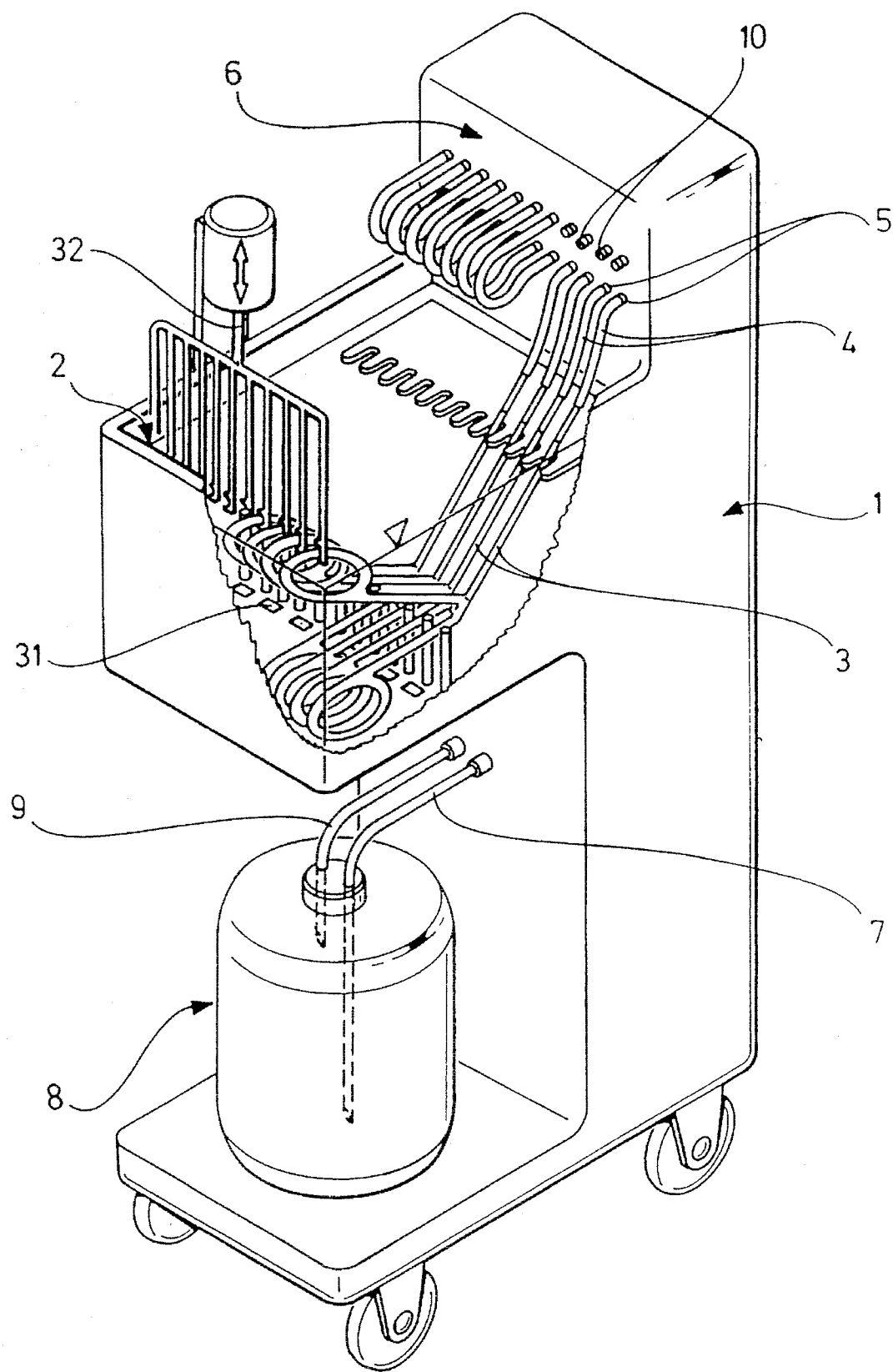
FIG. 1: shows a perspective view of a first, preferred embodiment of a cleaning device for medical instruments having a channel-like cavity.

The embodiment of a cleaning device illustrated in FIG. 1 comprises a portable housing 1 with an open container 2 for liquids, which is filled with a cleaning liquid.

A plurality of medical instruments 3, for example so-called tubular shaft instruments, are held in the interior of the container 2 on a suitable holder not illustrated in the drawing. These instruments are dipped into the liquid in the container such that their handle part and a large part of the shaft attached thereto dip into the liquid while the free end projects out of the liquid. A respective hose 4 is pushed sealingly onto this free end, for example, a silicone hose which leads to a respective connection in a console 6 arranged above the container 2 for liquids. A suction chamber which is not specifically outlined in the drawing is arranged within the console and communicates via a line 7 with a collection vessel 8 which is placed underneath the container 2 for liquids and is freely accessible from the front on the housing 1. The interior of the collection vessel 8 is connected via an additional line 9 with a suction pump arranged in the interior of the housing 1 and not illustrated in the drawing.

A respective blind plug 10 is held on the console 6 above each connection 5 and the respectively associated hose 4 is pushed onto the plug with its free end such that it is closed when it is not attached to an instrument 3. In the drawing, the hoses 4 on the left-hand side of the console are sealingly attached to the plugs 10 whereas on the right-hand side they are pushed onto instruments 3.

Inlet openings 31 are located at the base of the container 2 for liquids beneath the instruments 3 and a gas, preferably air, can be introduced into the container 2 through these openings via a device not illustrated in the drawing. These gas bubbles rise in the cleaning liquid in the region of the suction openings of the instruments 3 and lead to a turbulence in the cleaning liquid.

A motor drive 32 is represented only schematically in FIG. 1 and this engages all the instruments and periodically moves the movable parts of the instruments 3 relative to one another during the cleaning process, for example via an eccentric drive. In the illustrated embodiment, the two branches of the tubular shaft instruments are periodically opened and closed.

During operation, the instruments to be cleaned are dipped in the manner described into the cleaning liquid of the container 2 to such an extent that the greatest part is arranged beneath the level of the liquid. Hoses 4 are attached to the part projecting upwardly out of the liquid so that when the suction pump is switched on a vacuum is generated in the collection vessel 8. This leads to the cleaning liquid being drawn through the respective instrument 3 by suction, whereby the cleaning liquid can enter not only through the shaft end but through all the other openings which can result, for example, in joints or other gaps. This cleaning liquid is drawn by suction through the instrument 3 and the hose 4 into the collection vessel 8 so that, in this way, a thorough cleaning of the interior of the instrument 3 can take place.

The cleaning action can be improved, on the one hand, in that turbulences, which also continue in the interior of the cleaned tubular shaft instrument, are generated in the cleaning liquid due to gas bubbles being added and, on the other hand, due to the periodic movement of the movable parts of the instrument relative to one another. This ensures that the liquid circulates completely around all the regions of the instrument.

After termination of the cleaning, the hose 4 is withdrawn from the respective instrument 3 and pushed onto the associated plug so that no bypass occurs, through which the infiltrated air is drawn in by suction. The suction power is therefore concentrated to its full extent only on the respectively connected instruments 3.

In the embodiment of FIGS. 2 to 5, a holder 11 is provided which also takes over, at the same time, some of the tasks of the housing 1 in the embodiment of FIG. 1. The holder 11 comprises a lower part 12 with a support surface 13 for medical instruments which extends essentially horizontally, is partially covered with an elastomeric knobbed mat 14 and has additional openings 15 for the insertion of tubular shaft instruments.

The support surface 13 is borne via vertical side walls 16 on a base, on which the holder is placed.

An upper part 18 is mounted on the side walls 16 for pivoting about a horizontal axis 17. This upper part bears on two parallel arms 19 a suction chamber 20 which extends parallel to the axis 17 and is in the form of a tube extending over the entire width of the upper part 18. This suction chamber 20 communicates with a suction source via a short connection pipe 21 (FIG. 4), for example in the same manner as that explained in connection with the suction chamber of the embodiment of FIG. 1. The short connection pipe 21 can also be connected to a conventional secretion suction device which is used in operating theaters for drawing off body fluids and body secretions by suction.

The tubular suction chamber 20 bears next to one another a larger number of hand-operable closure valves 22 which are each connected to the interior of the suction chamber 20 and have a hose 23 connected to each of them.

Figure 2:
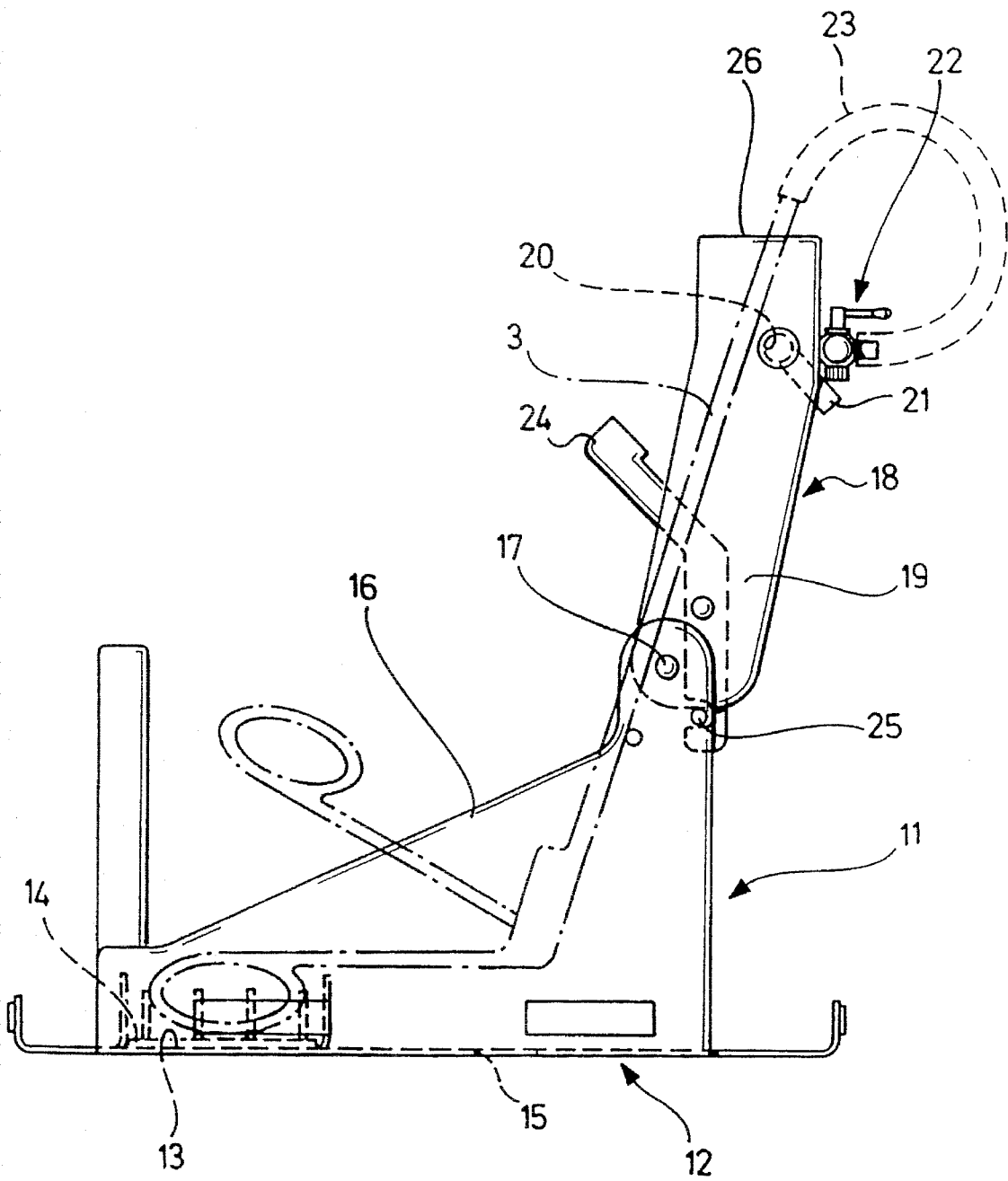
FIG. 2: shows a modified embodiment of a cleaning device with a holder for the instruments to be cleaned.
Figure 3:
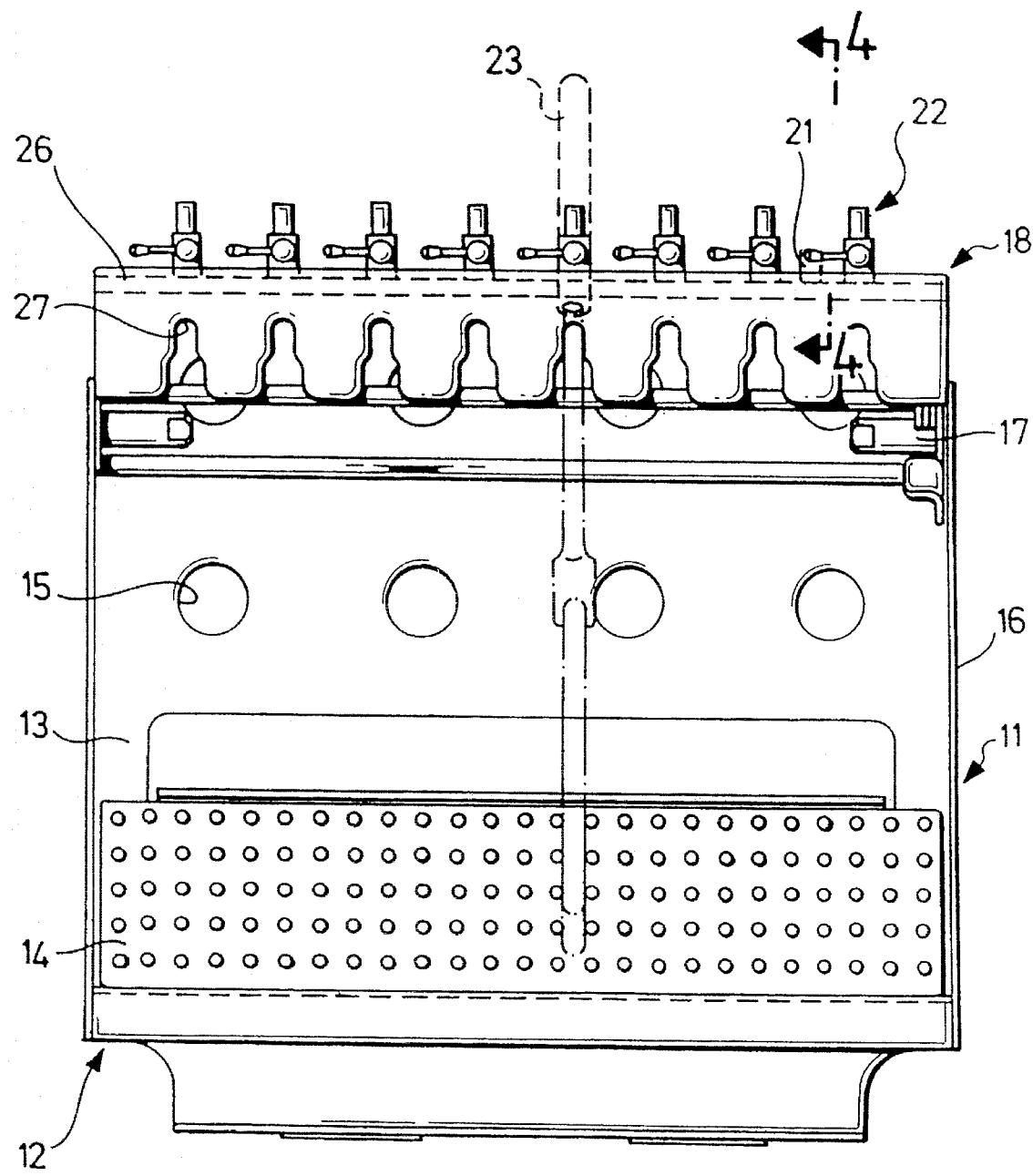
FIG. 3: shows a plan view onto the device of FIG. 2.
Figure 4:
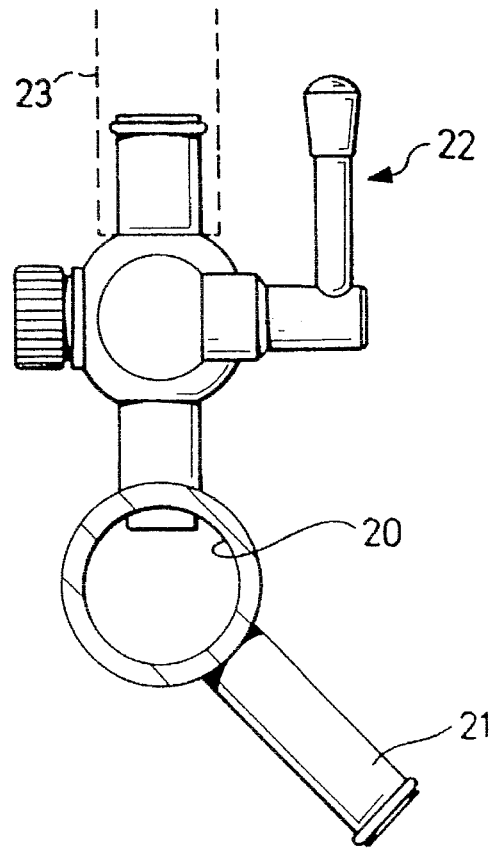
FIG. 4: shows a cross-sectional view along line 4—4 in FIG. 3.
Figure 5:
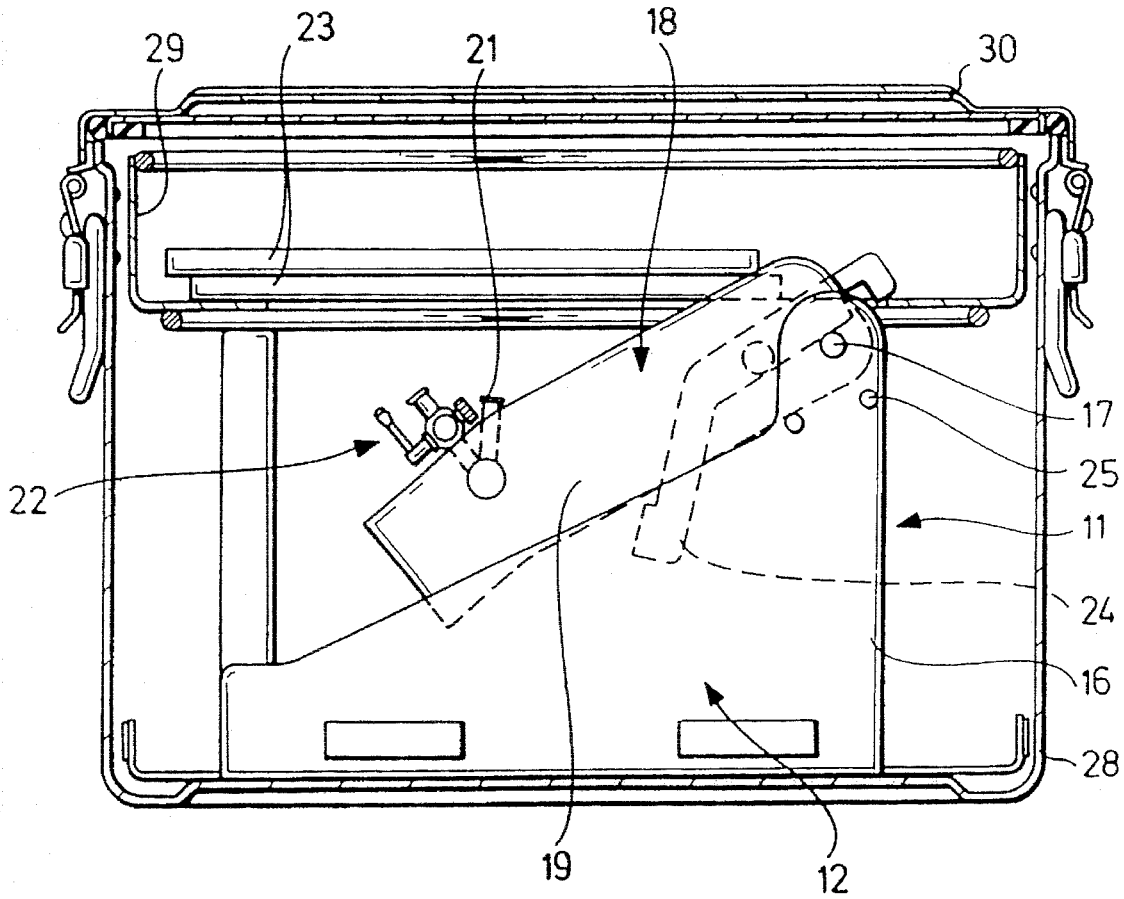
FIG. 5: shows a cross-sectional view of a container for accommodating the device of FIG. 2.

The upper part 18 can be pivoted downwards in the direction towards the lower part 12 so that a low overall height of the holder 11 results as a whole; this inoperative position is illustrated in FIG. 5. The holder reaches the operative position when the upper part 18 is pivoted upwards essentially vertically, as illustrated in FIG. 2. In this position, the upper part 18 is secured in position relative to the lower part 12 by a locking lever 24 which is pivotally mounted on an arm 19 of the upper part 18 and engages behind a projection 25 on the side wall 16 of the lower part 12. The locking lever 24 is held by a spring not illustrated in the drawing in a position in which any pivoting of the upper part 18 into the inoperative position is prevented when the locking lever 24 is pivoted into its end position under the action of the spring. The locking lever 24 can be pivoted contrary to the action of the spring and then releases the projection 25; in this position of the locking lever 24, the upper part 18 can be pivoted into the inoperative position.

Several recesses 27 are arranged next to one another on the front side 26 of the upper part 18, namely each closure valve 22 has its own recess 27 associated with it. The recesses 27 are formed in the illustrated embodiment by longitudinal slots narrowing in steps and open towards the lower side of the upper part 18. Instruments 3 placed on the support surface 13 can be inserted into these longitudinal slots 27 so that the instruments 3 take up a defined position on the holder, whereby a respective instrument 3 is associated with each closure valve 22 and, therefore, with each hose 23.

In the inoperative position, the holder 11 has a relatively low overall height so that it can be inserted into the tub-shaped lower part 28 of a box-shaped container, into which an insert 29 in the form of a sieve tray is also inserted above the holder 11 (FIG. 5). A cover 30 is sealingly placed on the lower part 28. The container consisting of lower part 28 and cover 30 is designed in the manner of a sterilizer; it therefore consists of metal and is also adapted in its dimensions preferably to the customary dimensions of a sterilizer. The sieve tray 29 normally accommodates the hoses 23.

During operation, the sieve tray 29 with the hoses is taken out of the container; subsequently, the hoses 23 are attached to the respective closure valves 22.

The holder 11 is placed in the lower part 28 of the container with the upper part 18 in operative position; this lower part 28 is filled with the cleaning liquid. Prior to filling or thereafter, the instruments to be cleaned are inserted into the holder 11, whereby they are secured in position on the knobbed mat 14 or in the openings 15, on the one hand, and in the recesses 27, on the other hand. The hoses 23 are pushed onto the ends of the instruments 3 projecting out of the liquid. Only when the hoses are attached are the closure valves 22 subsequently opened by hand so that cleaning liquid can be drawn through the instruments 3 into the suction chamber 20 by suction via the short connection pipe 21 and the vacuum source connected thereto.

The container illustrated in FIG. 5 with the inserted holder therefore accommodates all the components necessary for the cleaning of the instruments and can, at the same time, be used as cleaning container; it is merely necessary to connect the entire device to a customary vacuum source via the short connection pipe 21.

We claim:

1. A device for cleaning medical tubular shaft instruments having a handle and a free end, said device comprising:

a container for holding a cleaning bath of a cleaning liquid;

a holder for holding the tubular shaft instruments such that said handle portion and at least a portion of a shaft attached thereto dip into the cleaning bath in said container;

a suction chamber arranged at an upper portion of the holder, said suction chamber bearing a number of closure means next to one another; and hoses connected individually to each closure means;

wherein each of said hoses is sealingly attachable to said free end of a corresponding one of the tubular shaft instruments to provide a suction force at said free end;

thereby allowing cleaning liquid to be drawn from said cleaning bath through the shaft of the instrument, and then through said free end.

2. A device as defined in claim 1, wherein the closure means comprises a hand-operable closure valve.

3. A device as defined in claim 1, wherein the closure means for each hose comprises a plug secured in position on the device, a free end of the hose being sealingly attachable to said plug.

4. A device as defined in claim 1, wherein said holder comprises at least two parts movable relative to one another between an operative position having a large overall height and an inoperative position having a low overall height.

5. A device as defined in claim 4, wherein said at least two parts are securable relative to one another in the operative position.

6. A device as defined in claim 4, wherein one of said at least two parts is an upper part that is pivotable relative to the other of said parts, which is a lower part of the holder.

7. A device as defined in claim 4, wherein said container is closable by means of a cover and is dimensioned such that it completely accommodates the holder at least in the inoperative position.

8. A device as defined in claim 7, wherein a removable insert is arranged in the container above the holder and said hoses are adapted to be placed in said insert.

9. A device as defined in claim 1, wherein said container is closable by means of a cover and is dimensioned such that it completely accommodates the holder at least when the device is not in use.

10. A device as defined in claim 9 wherein removable insert is arranged in the container above the holder and said hoses are adapted to be placed in said insert.

11. A device as defined in claim 1, wherein at least one gas inlet is provided in said container beneath the tubular shaft instruments dipping into the cleaning liquid, enabling gas to enter the cleaning liquid beneath the tubular shaft instruments.

12. A device as defined in claim 1, wherein a drive is provided for engaging the tubular shaft instruments and moving parts of the tubular shaft instruments relative to one another.

13. A device as defined in claim 1, wherein said tubular shaft medical instrument is a forceps.

14. A method for cleaning medical tubular shaft instruments having an end with a handle and a free end, comprising the steps of:

providing a cleaning bath of a cleaning liquid;

dipping said end with said a handle of each tubular shaft instrument into the cleaning bath such that said handle together with part of a shaft attached thereto is immersed in the cleaning bath;

sealingly pushing a suction hose onto said free end;

applying a suction force at said free end via said suction hose;

drawing cleaning liquid from said cleaning bath through the shaft of the instrument, and then through said free end and into the suction hose; and receiving the cleaning liquid in said suction hose after it is drawn through the instrument.

15. A method as defined in claim 14 wherein a plurality of said tubular shaft instruments are cleaned simultaneously, comprising the further steps of:

providing a separate suction hose for each of the instruments;

connecting each suction hose to a common suction line;

sealingly pushing each suction hose onto the free end of a respective one of the instruments;

opening individual connections between each suction hose and said common suction line to provide a suction force at said respective free ends.

16. A method as defined in claim 15 comprising the further step of:

introducing gas bubbles into said cleaning bath such that the gas bubbles rise in the cleaning liquid and are drawn into the instrument during said drawing step.

17. A method as defined in claim 15 comprising the further step of:

moving parts of said handle relative to one another during said drawing step.

18. A method as defined in claim 14 comprising the further step of:

introducing gas bubbles into said cleaning bath such that the gas bubbles rise in the cleaning liquid and are drawn into the instrument during said drawing step.

19. A method as defined in claim 14 comprising the further step of:

moving parts of said handle relative to one another during said drawing step.

20. A method as defined in claim 14, wherein said tubular shaft medical instrument is a forceps.

\* \* \* \* \*